(12) United States Patent
Divi et al.

(10) Patent No.: US 8,569,514 B1
(45) Date of Patent: Oct. 29, 2013

(54) PROCESS FOR THE PREPARATION OF STRONTIUM RANELATE

(75) Inventors: Murali Krishna Prasad Divi, Hyderabad (IN); Mysore Aswatha Narayana Rao, Hyderabad (IN); Shaik Nowshuddin, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 0 days.

(21) Appl. No.: 13/603,896

(22) Filed: Sep. 5, 2012

(30) Foreign Application Priority Data

May 17, 2012 (IN) ............................ 1969/CHE/2012

(51) Int. Cl.
C07D 333/38 (2006.01)
C07D 333/40 (2006.01)
(52) U.S. Cl.
USPC ............................................................ 549/61

(58) Field of Classification Search
USPC ............................................................ 549/61
See application file for complete search history.

(56) References Cited

U.S. PATENT DOCUMENTS

| 5,128,367 A | 7/1992 | Wierzbicki et al. |
| 2006/0069271 A1 | 3/2006 | Horvath et al. |
| 2011/0275834 A1 | 11/2011 | Divi |

FOREIGN PATENT DOCUMENTS

| WO | 2007020527 A2 | 2/2007 |
| WO | 2010034806 A1 | 4/2010 |
| WO | 2011086399 A1 | 7/2011 |

*Primary Examiner* — Noble Jarrell
*Assistant Examiner* — Valerie Rodriguez-Garcia
(74) *Attorney, Agent, or Firm* — Caesar. Revise, Bernstein, Cohen & Pokotilow, Ltd.

(57) ABSTRACT

Strontium ranelate is prepared by reacting dicyclohexylammonium ranelate with strontium halide in an anhydrous solvent. Strontium ranelate thus obtained will have less than 3% moisture content.

14 Claims, No Drawings

PROCESS FOR THE PREPARATION OF STRONTIUM RANELATE

CROSS-REFERENCE TO RELATED APPLICATION

This application claims priority from India Application 1969/CHE/2012, filed May 17, 2012, entitled A PROCESS FOR THE PREPARATION OF STRONTIUM RANELATE of which the following is a specification, which application is assigned to the same assignee as this application and whose disclosure is incorporated by reference herein.

FIELD OF INVENTION

The present invention discloses a novel process for the preparation of strontium ranelate having less than 3% moisture content.

BACKGROUND OF THE INVENTION

Strontium ranelate is distrontium salt of 5-[bis(carboxymethyl)amino]-3-carboxymethyl-4-cyano-2-thiophenecarboxylic acid and is represented by formula:

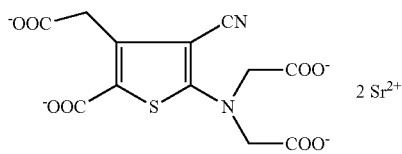

Strontium ranelate is used for treating osteoporosis and other bone diseases. It increases bone formation and also reduces bone resorption resulting in a rebalance of bone turnover in favor of bone formation.

DESCRIPTION OF THE INVENTION

The preparation of strontium ranelate is described in the U.S. Pat. No. 5,128,367. The "367" patent gives three methods to prepare strontium ranelate. In the first method, ranelic acid is dissolved in water and treated with strontium hydroxide to obtain strontium ranelate as octahydrate. In the second method the sodium salt of ranelic acid is dissolved in water and treated with strontium chloride. In the third method, the tetraethyl ester of ranelic acid is directly hydrolyzed with strontium hydroxide in an aqueous solution. In all the cases strontium ranelate is obtained as an octahydrate and contains about 20% moisture. The U.S. Pat. No. 7,459,568B2 describes an alpha crystalline form of strontium ranelate prepared by dissolving strontium ranelate in water followed by refluxing the solution and cooling. The alpha crystalline form is also an octahydrate with 22-24% of water. WO 2007/020527 A2 application describes a process for preparing strontium ranelate octahydrate from tetra ester through lithium base. WO 2011/086399 A1 describes another process where ammonium salt of ranelic acid is dissolved in water and treated with strontium halide to obtain strontium ranelate having characteristics similar to that described in prior art. Since, strontium ranelate is obtained from the aqueous medium, the salt is an octahydrate.

Strontium ranelate is available in the market as "PROTELOS", which is a 2 g sachet containing granules of strontium ranelate. The daily recommended dose is 2 g as a single dose. The marketed "PROTELOS" contains strontium ranelate as its octahydrate. High moisture content of strontium ranelate, to the extent of about 22% indicates that only about 78% drug is available per unit weight. Since the dose is large, the bulk of the formulation is very large.

Those in the art would like to have strontium ranelate with lower moisture content so that the size of the formulation can be minimized. There is thus a need for strontium ranelate with low moisture content, which could be used in formulations.

The US patent application, US 2011/0275834 A1 describes a process for obtaining strontium ranelate having 1.5 to 2.5% water content by suspending the salt in a suitable solvent such as toluene, and refluxing to remove water by azeotropic distillation. A similar method is also reported in WO 2010/034806 A1. However, such azeotropic distillation at a high temperature results in the formation of impurities. According to 2010/034806 A1, when ranelic acid or strontium ranelate is heated, such as during azeotropic drying, des-carboxy ranelic acid and the strontium salt of des-carboxy ranelic acid are formed as impurities. Des-carboxy ranelic acid has the following formula:

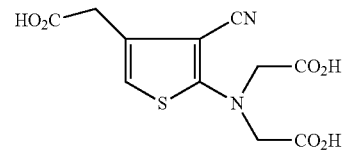 [SMILES: N#Cc1c(CC(=O)O)csc1N(CC(=O)O)CC(=O)O]

Hence there is a need for a better method to prepare strontium ranelate with low moisture content by using milder conditions which does not result in the formation of impurities.

SUMMARY OF THE INVENTION

The objective of the present invention is to develop a process for strontium ranelate having less than 3% moisture content. It is difficult to prepare completely anhydrous form because the strontium halide or strontium hydroxide used in preparing the salt contains certain amount of moisture.

All prior art processes use aqueous medium at the final stage of salt formation which results in high moisture content. Hence we used a strategy to carry out the salt formation in an anhydrous medium. We envisaged that a ranelic acid salt with an organic non-polar base will be water insoluble, but soluble in an organic solvent. Such a salt, dissolved in a non-aqueous organic solvent can undergo "salt exchange" with stronger strontium halide. We have now found that the dicyclohexylamine (DCHA) forms a salt with ranelic acid, which is insoluble in water but soluble in organic solvent such as methanol and on reaction with strontium halide at ambient temperature, gives strontium ranelate, whose moisture content is less than 3%. It is also observed that isolation of ranelic acid as a DCHA salt helps in improving the purity. Since the process of strontium salt formation takes place at ambient temperature without subjecting to very high temperatures, formation of impurities due to degradation are avoided.

DETAILED DESCRIPTION OF THE INVENTION

Ranelic acid is dissolved in a suitable organic solvent, and the solution is treated with DCHA. The solvents which can be used are ethers such as diisopropyl ether, esters such as ethyl acetate, chlorinated hydrocarbons such as dichloromethane, ketones such as acetone, aprotic solvents such as tetrahydrofuran, acetonitrile and dimethylformamide. The solution is stirred at temperature of 5 to 40° C., preferably 20±5° C. Within few minutes of stirring, precipitation of dicyclohexylammonium ranelate starts. Stirring can be continued for a few hours to complete the precipitation. The precipitated salt is collected by filtration. The salt is washed with the same solvent to remove traces of free DCHA or ranelic acid. It is dried under reduced pressure till the moisture content is less than 0.5%. This process gives the DCHA salt in very high yields (>90%) and purity (>99.5%).

Since ranelic acid has four carboxylic groups, it can react with four moles of DCHA. However, analysis of the salt shows that one mole of ranelic acid reacts with two moles of DCHA.

The preparation of strontium ranelate consists of dissolving strontium DCHA salt in a suitable solvent and reacting with strontium halide.

The suitable solvents for dissolving DCHA salt of ranelate are alcohols preferably methanol, esters such as n-butyl formate and aprotic solvent such as dimethylformamide. These are also ideal solvents because of good solubility of strontium halides in these solvents. Strontium halide is a salt of a strong acid and undergoes salt exchange with dicyclohexylammonium ranelate in a facile manner. Of the available strontium halides, strontium chloride is preferred because it is inexpensive and easily available. Strontium chloride is available as a monohydrate and in anhydrous form commercially. It is important to use the anhydrous form. If hydrated form is to be used, it should be made anhydrous by azeotropic drying. The moisture content of strontium chloride used must be less than 0.5% (by KF method). The solvent used must also be anhydrous. As soon as the solution of DCHA salt of ranelate reacts with strontium halide, precipitation of strontium ranelate takes place. Stirring for a few hours results in complete precipitation. The precipitate is filtered and washed with a small amount of solvent to remove traces of starting materials. The strontium ranelate obtained is in high yields and purity (>94% Y; >99.5% HPLC, MC: <3.0%).

The embodiments of the present invention are illustrated in the following examples, which are not intended in any way to limit the scope of the invention. One skilled in the art can easily modify the details to suit the inputs and desired outcomes without affecting the present invention.

Example-1

Ranelic acid (10.0 g, 0.029 mol) was dissolved in acetone (100 ml) at 25±5° C. to get a clear solution. To this solution was added dicyclohexylamine (13.2 g, 0.0731 mol) while stirring. After 5 hours stirring, the precipitated salt of dicyclohexylammonium ranelate was collected by filtration. The solid was washed with a small amount of acetone and dried at room temperature (Yield: 18.6 g, 90.4%; purity: 99.5% HPLC).

Example-2

Ranelic acid (10.0 g, 0.029 mol) was dissolved in acetonitrile (100 ml) at 25±5° C. to get a clear solution. To this solution was added dicyclohexylamine (13.2 g, 0.0731 mol) while stirring. After 3 hours stirring, the precipitated salt of dicyclohexylammonium ranelate was collected by filtration. The solid was washed with a small amount of acetonitrile and dried at room temperature (Yield: 19.3 g, 94%; purity: 99.5% HPLC).

Example-3

Dicyclohexylammonium ranelate (20 g, 0.028 mol) was dissolved in methanol (100 ml). Separately strontium chloride (11.3 g, 0.071 mol) was dissolved in methanol (100 ml, 0.14% MC) and was added to the solution of dicyclohexylammonium ranelate at 25±5° C. while stirring. After 5 hours stirring, the precipitated salt of strontium ranelate was collected by filtration. The solid was washed with methanol (10 ml×2) and dried under vacuum at room temperature (Yield: 13.3 g, 88.7%; purity: 99.7% HPLC, MC: 1.7%).

Example-4

Dicyclohexylammonium ranelate (20 g, 0.028 mol) was dissolved in dimethylformamide (200 ml, 0.12% MC). Strontium chloride (11.3 g, 0.071 mol) was added portion wise to the dimethylformamide solution at 25±5° C. while stirring. After 5 hours stirring, the precipitated salt of strontium ranelate was collected by filtration. The solid was washed with methanol (50 ml) and dried under vacuum at room temperature (Yield: 12.2 g, 82%; purity: 99.4% HPLC, MC: 2.2%).

We claim:

1. A process for the preparation of strontium ranelate having less than 3% moisture content which comprises:
    a) reacting ranelic acid with dicyclohexylamine in an anhydrous solvent to obtain dicyclohexylammonium ranelate salt; and
    b) reacting the dicyclohexylammonium ranelate salt with strontium halide in an anhydrous solvent to obtain strontium ranelate.

2. The process according to claim 1, step-a, wherein the anhydrous solvent used is selected from the group consisting of ethers, esters, chlorinated hydrocarbons and ketones.

3. The process according to claim 2, step-a, wherein the ether is methyl tert-butyl ether.

4. The process according to claim 2, step-a, wherein the ester is ethyl acetate.

5. The process according to claim 2, step-a, wherein the chlorinated hydrocarbon is dichloromethane.

6. The process according to claim 2, step-a, wherein the ketone is acetone.

7. The process according to claim 1, step-a, wherein the anhydrous solvent is selected from the group consisting of tetrahydrofuran and acetonitrile.

8. The process according to claim 1, step-b, wherein the anhydrous solvent used is selected from the group consisting of alcohols and esters.

9. The process according to claim 8, step-b, wherein the alcohol is methanol.

10. The process according to claim 8, step-b, wherein the ester is butylformate.

11. The process according to claim 1, step-b, wherein the anhydrous solvent is dimethylformamide.

12. The process according to claim 1, step-b, wherein strontium halide used is strontium chloride.

13. The process according to claim 12, wherein strontium chloride used has moisture content of less than 1%.

14. Dicyclohexylammonium ranelate salt having dicyclohexylamine and ranelic acid in a ratio of 2:1.

* * * * *